United States Patent [19]

Harte et al.

[11] 4,163,779

[45] Aug. 7, 1979

[54] TEST FOR QUANTITATION OF IMMUNOGLOBULIN AND IDENTIFICATION OF ABNORMAL IMMUNOGLOBULIN

[75] Inventors: Richard A. Harte, Redwood City; Fred H. Deindoerfer, Santa Clara, both of Calif.

[73] Assignee: International Diagnostic Technology, Inc., Santa Clara, Calif.

[21] Appl. No.: 868,189

[22] Filed: Jan. 9, 1978

[51] Int. Cl.$^2$ .................... G01N 33/16; A61K 39/00; A61K 43/00

[52] U.S. Cl. ...................................... 424/1; 23/230 B; 424/8; 424/12

[58] Field of Search .................... 424/1, 12; 23/230 B

[56] References Cited

U.S. PATENT DOCUMENTS 4,091,089  5/1978  Chichibo et al. .................. 23/230 B

*Primary Examiner*—Benjamin R. Padgett
*Assistant Examiner*—Christine M. Nucker

*Attorney, Agent, or Firm*—Limbach, Limbach & Sutton

[57] ABSTRACT

A combined test for quantitating immunoglobulin and identifying the presence of abnormal homogeneous immunoglobulin usually of myeloma origin. In a direct test, a first fraction of serum sample is adsorbed to a solid surface and the adsorbed immunoglobulin is reacted with labeled antibody and the quantity of labeled antibody on the surface is measured. A second fraction of the serum sample is subjected to a competitive test in which normal immunoglobulin is adsorbed onto a second solid surface. Then, specific labeled antibody is competitively immunologically reacted with the immunoglobulin adsorbed on the surface and sample immunoglobulin. After washing, the labeled antibody on the second surface is measured to provide a quantitative measurement of sample immunoglobulin. Abnormal immunoglobulin is indicated if the ratio of immunoglobulin content of the sample as found by the competitive test to the quantity found by the direct test is 2:1 or greater.

5 Claims, No Drawings

TEST FOR QUANTITATION OF IMMUNOGLOBULIN AND IDENTIFICATION OF ABNORMAL IMMUNOGLOBULIN

CROSS-REFERENCE TO RELATED APPLICATIONS

Reference is made to application Ser. No. 658,298 filed Feb. 17, 1976, entitled "Method for Quantitation of Antigens or Antibodies on a Solid Surface", in the name of Gunner (NMI) Bolz, et al., and to application Ser. No. 684,775 filed May 10, 1976, entitled "Competitive Fluorometric Immunoassay Solid Surface Technique".

BACKGROUND OF THE INVENTION

The serum of a healthy patient includes at least five classes of normal immunoglobulin: IgG, IgA, IgM, IgD, and IgE. Normal immunoglobulins are polyclonal, i.e., characterized by heterogeneity within each class. In a myeloma patient, one clone of plasma cells proliferates inordinately produced one homogeneous monoclonal immunoglobulin in excessive amounts. Since the presence of such excess homogeneous immunoglobulins is symptomatic of myeloma, they are referred to as abnormal immunoglobulins. The presence of such abnormal immunoglobulins can be qualitatively determined by known techniques such as serum protein electrophoresis (SPE). To quantitate the immunoglobulins, SPE must be employed in conjunction with a quantitative test, such as radial immunodiffusion (RID) or electroimmunoquantitation (EIP). This combination of tests is tedious and time consuming. It should be desirable to accomplish the objectives of these tests in a rapid and efficient manner.

SUMMARY OF THE INVENTION AND OBJECTS

A combination of direct and competitive immunological solid surface tests labeled as with a fluorogen are employed to quantitate immunoglobulins in serum and also as a qualitative test for abnormal immunoglobulins. In the direct portion of the test, a sample, such as serum, is first sorbed to a solid surface and immunologically reacted with labeled antibody. After washing, the quantity of reacted labeled antibody is measured. In the competitive test, normal heterogeneous immunoglobulin of the same class as the sample immunoglobulin is sorbed into a second solid support surface. Then specific labled antibody is reacted with the immunoglobulin on the second surface and with the immunoglobulin in another fraction of the sample. After washing, this surface is also measured for reacted labeled antibody. It has been found that if the sample contains abnormal immunoglobulin, then the direct test indicates only a fraction of the total immunoglobulin content. The competitive test, however, gives a measure of total immunoglobulin in the sample whether or not abnormal homogeneous immunoglobulin is present. If the ratio of immunoglobulin measured by the competitive test to immunoglobulin measured by the direct test is 2:1 or higher, then abnormal immunoglobulin is present.

It is an object of the invention to provide a rapid, efficient solid surface test for the quantitation of immunoglobulins and the qualitative detection of abnormal immunoglobulins.

It is a further object of the invention to provide such a test using labeled antibody.

It is another object of the invention to provide such a test for the ratio of abnormal immunoglobulins to normal immunoglobulins within the same class.

Further objects and features of the invention will be apparent from the following description of its preferred embodiments.

DETAILED DESCRIPTION OF THE PREFERRED EMBODIMENTS

The present invention relates to the employment of both a direct test and a competitive test for the quantitation on a solid support surface of immunoglobulin in a serum sample and to the aualitative detection of abnormal immunoglobulin. The direct solid surface test will first be described. Only a small portion of abnormal immunoglobulin present in the sample is detected in this test. Thereafter, the competitive test is described using another fraction of the same sample. This test accurately quantitates the total of abnormal and normal immunoglobulin. When the ratio of the immunoglobulin in a class detected by the competitive test in comparison to the direct test is in excess of 2:1, the presence of abnormal immunoglobulin is indicated.

Direct Test

Briefly summarized, the direct test may be performed by the following sequence of steps. A first fraction of serum immunoglobulin is adsorbed directly onto a solid support surface. The test will be described with reference to determination of IgG. After removal of unadsorbed sample, the surface is exposed to reagent containing labeled specific antibody immunologically reactive with the sample IgG to cause the immunological reaction to occur. Thereafter, unreacted labeled antibody is removed from the surface and quantity of reacted labeled antibody is measured. Prior to the adsorption step, a predetermined quantity of buffer protein unreactive with labeled antibody may be added to the sample to minimize the dependence of IgG quantitation on the variations in concentrations of other protein in the sample.

In a typical instance, a serum sample is obtained by collecting blood without anticoagulant by conventional procedures and allowing the blood to clot.

In the first step of the procedure, the protein of the blood serum is sorbed, preferably by physical adsorption, to an immunologically unreactive solid support surface adsorptive for the IgG. A suitable technique of adsorption is immersion of the support surface in a test tube of serum sample, and mixing the same thoroughly, as with an automatic shaker, for approximately 20 minutes.

A suitable solid support surface is formed of a water-insoluble polymeric material sorptive for the antigen. Known materials of this type include hydrocarbon polymers such as polystyrene, polyethylene, polypropylene, polybutylene, butyl rubber and other synthetic rubbers. Other suitable organic polymers include silastic rubber, polyesters, polyamides, cellulose and celluloxid derivatives, acrylates, methacrylates, and vinyl polymers such as polyvinyl chloride, and polyvinyl fluoride. In addition to the foregoing materials, the solid support surface may comprise silica gel, silicone wafers, glass, insoluble protein, and metallic surfaces (e.g., tantalum coated glass).

A particularly effective solid support surface is a disc, formed of polymethylmethacrylate film. After completion of the reactions described hereinafter, the technique of reading the labeled substance on the support surface may follow the detection technique set forth in application Ser. No. 627,941, filed Nov. 3, 1975, entitled "Diagnostic Reagent Holder and Method".

In a blood serum sample, the total protein content may vary from about 3 to 12%. The basis of the quantitation of the immunoglobulin to be detected is that the amount of immunoglobulin adsorbed onto the surface is proportional to its concentration in the serum sample. This assumes that the concentrations of the other substances in the serum that adsorb onto the surface remain essentially constant and that the surface is relatively nonspecific with respect to the different adsorbed substances, predominantly proteins. Neither of these assumptions is totally accurate. (L. Vroman, et al., *Advances in Chemistry Series*, No. 45 (1976)). However, variations in the above factor underlying these assumptions that may effect accurate quantitation may be minimized as follows.

It is apparent that the immunoglobulin to be quantitated competes with other protein in the serum for adsorption sites on the support surface. The term "other protein", as used herein, refers to the protein content other than the immunoglobulin to be measured in the liquid sample. Thus, variation in the quantity of such other protein will vary the amount of adsorbed antigen resulting in errors in quantitation of immunoglobulin. It has been found that this source of error can be reduced to a minimum by the addition to the serum sample prior to adsorption of a predetermined quantity of buffer protein, unreactive with the labeled antibody, at a concentration sufficient to minimize the dependence of adsorbed immunoglobulin upon the variable content of the other protein in the sample. The term "buffer protein" refers to protein added to the original sample which is unreactive with the subsequently added labeled antibody and which minimizes the effect of variation in the final quantitation caused by the variation of other protein. Preferably, the ratio of buffer protein to total protein in the serum or other protein is in excess of 1:1 by weight. The effect of buffer protein is illustrated by added, say, a ten fold excess over other protein. In the instance, variation of other protein in the sample would not vary the adsorbed antigen to any significant extent.

The buffer protein solution comprises a stable adsorbable protein which is unreactive with the specific antibody for the immunoglobulin to be detected. A suitable solution for this purpose comprises a 0.125% by weight solution of bovine serum albumin in phosphate buffered saline at a pH of 7.5.

The foregoing Vroman publication reports that there is some variation in the adsorption affinity of various proteins for different polymeric surfaces or different types of samples were employed as a reference. Accordingly, calibration of a reference curve should utilize the same type of support surface and the same of sample, e.g., serum or equivalent, and the same buffer protein solution to minimize the effect upon quantitation of this variation in adsorption affinity.

After adsorption of serum IgG, the surface is washed with an appropriate solution to remove unadsorbed components of the serum sample. The aforementioned buffer protein solution is an example of such an appropriate solution. After washing, the support surface containing IgG is exposed to an excess of a labeled specific antibody immunologically reactive with IgG to cause an immunological reaction to occur on the surface. The duration of the immunological reaction step should be sufficient for completion of the reaction. A suitable time for this purpose is on the order of 5 minutes to two hours during which the sample is constantly mixed as by shaking.

Any conventional labeling substance may be attached to the antibody to be reacted with the immunoglobulin on the surface. Such labeled substance may include a luminescent substance such as a phosphor or fluorogen, a radioactive substance, an enzyme, or a metal containing substance.

After completion of the immunological reaction, the support surface is washed in a buffer solution to remove unreacted labeled antibody from the surface which could interfere with the quantitation. An effective washing solution comprises phosphate buffered saline solution.

After washing, the surface is read in an appropriate reading device. The present system is particularly adapted for fluorescent detection on the surface of a diagnostic reagent holder of the type set forth in the aforementioned U.S. Pat. No. 3,999,948. Thus, the holder containing the fluorescently labeled disc is placed into a viewing housing for reading by a fluormeter. Such readings can be taken in less than 10 seconds.

The aforementioned fluorometric readings are compared against known reference preparations adsorbed similarly upon identical surfaces. For example, for the specific immunoglobulin to be read, calibration curves are prepared for different concentrations of immunoglobulin versus the fluorescent signal in arbitrary units. As guidance, the assay ranges for routine methodology of serum samples are as follows: IgG—300 to 2,000 mg/dl; IgA—35 to 480 mg/dl; and IgM—15 to 400 mg/dl.

Suitable fluorescent labels include lissamine-rhodamine B, D.A.N.S. (1-dimethylamino-naphthalene-5-sulfonic acid), orthophthaladehyde, fluorescein isothiocyanate and fluorescamine, which are frequently used in fluorescent microscopy. The first two possess a blue or green emission spectra. The only variation in the fluorometer would be the change in excitation and emission fliters used, as well as the changes in the fluorescent tag on the antibodies in the reagent kit.

When the label comprises a radioactive substance, a suitable reading device is a scintillation counter.

The present technique is also applicable to the use of enzyme labeled systems. One such system is described in an article by Pesce et al. entitled "Use of Enzume-Linked Antibodies to Measure serum Anti-DNA Antibody in Systemic Lupus Erthyematosus", Clin. Chem. 20/3, 353–359 (1974). The described system differs from the one described herein in that the diagnostic reagent, DNA, is adsorbed to a test tube support. Thereafter, anti-DNA antibody containing serum is reacted with the coated tube followed by reaction with an anti-human gamma globulin peroxidase enzyme conjugate. Then a colored reaction product is developed by action of peroxidase on a substrate which is colorimetrically measured by conventional techniques.

The present solid surface technique is preferably performed with a fluorescently labeled antibody. An effective reagent is a fluorescein isothiocyanate (FITC) labeled monospecific antibody to human IgG, IgA, or IgM in a buffered saline solution. Fluorexcent labeling permits quantitation using a fluorometer reading a precise predetermined area comprising only reaction support surface. This can be accomplished by viewing such surface through a window of a viewing housing framed by opaque material which permits detection of fluorescence emitted only from the surface. This would be difficult to accomplish with a radioactively labeled substance. A particularly effective viewing housing and reaction support surface is illustrated in the aforementioned U.S. Pat. No. 3,999,948, incorporated herein by reference. The support surface comprises the disc attached to the diagnostic reagent holder of said application. The importance of viewing only the support surface is that there is a degree of carryover of labeled substance which attaches to the holder in addition to that which attaches to the disc. This is a particular problem in the present direct technique in which the sample protein may adsorb relatively nonspecifically in significant quantities to the holder as well as the disc, especially if the holder is formed of a polymer adsorptive for protein.

Although physical adsorption is preferred as the sorption technique employed in the direct method because of its simplicity and the inexpensive nature of the support surface, it should be understood that other sorption techniques may be employed within the scope of the present invention. For example, specially treated ion exchange resins may be employed as the surface for ionic bonding of the immunoglobulin to be measured.

Competitive Technique

A second fraction of the serum immunoglobulin to be tested is analyzed in a competitive technique which may be performed by the following sequence of steps using a second fraction of the same serum immunoglobulin used in the first test. A reagent comprising normal heterogeneous immunoglobulin (IgG) is adsorbed onto another solid support surface of the foregoing type. After washing, specific labeled antibody for the adsorbed IgG is competitively immunologically reacted with the same and with the serum sampel IgG. In this manner, the labeled antibody on the second surface is inversely related to the concentration of IgG in the second sample fraction. After washing, the quantity of reacted labeled antibody on the surface is measured to provide an accurate determination of the amount of total normal and abnormal IgG of the indicated class.

In the first step of the competitive procedure, a normal heterogeneous immunoglobulin of the same class as the immunoglobulin to be measured in the serum is physically adsorbed onto the support surface by immersion in a test tube of a pooled human serum which has been standardized against WHO international reference preparations. Such standardized serum samples will be designated herein as calibrators. The support surface is mixed thoroughly with the calibrator, as with an automatic shaker, for approximately 20 minutes.

After adsorption of IgG from the calibrator, the surface is washed with an appropriate solvent to remove unadsorbed components of the serum sample. The aforementioned buffer protein solution is an example of such an appropriate solution.

In another steps, a fraction of the serum sample containing IgG is incubated with an excess of labeled specific antibody immunologically reacted with IgG. The duration of incubation should be sufficient for completion of the immunological reaction. A suitable time for this purpose is on the order 10 to 30 minutes during which the sample is constantly mixed by shaking.

After the above incubation step, the support surface coated with IgG adsorbed from the calibrator is immersed and mixed in the incubated sample serum wherein the excess labeled antibody in the calibrator serum immunologically reacts with the adsorbed IgG for a sufficient time (e.g., 5 minutes to 2 hours) for completion of the reaction. The labeled antibody which immunologically reacts with the surface IgG is inversely related to the concentration of the IgG in the serum sample fraction. This is because only the excess free antibody which is not bound to IgG in the serum is capable of reacting with the IgG on the support surface. In other words, the reacted antibody on the support surface is a measure of such unbound antibody.

After completion of the above immunological reaction, the support surface is washed, as in a buffer solution, to remove unreacted labeled antibody from the surface which could interfere with the quantitation.

After washing, the surface is read with an appropriate reading device as in a fluorometer of the foregoing type.

The aforementioned fluorometric readings are compared against known reference preparations as by calibration curves of the foregoing type prepared in a competitive manner.

Any conventional labeled antibody as set forth with respect to the direct technique may be employed for the competitive technique.

In an alternative to the above sequential competitive technique, the IgG coated surface may be immersed in a mixture of serum and antibody prior to incubation for a simultaneous competitive immunological test.

It has been discovered that in the above direct technique, only a small portion of the abnormal immunoglobulin in the serum is detected by a fluorometer. It is theorized that this is due to an unexpected aggregation onto the support surface of the abnormal homogeneous immunoglobulin so that the labeled antibody can only combine with those abnormal molecules on the surface of the aggregates. This produces a significantly diminished fluorescent signal in comparison to that which would be obtained for a comparable heterogeneous immunoglobulin concentration.

In contrast to the direct technique, the above competitive technique quantitates both normal and abnormal immunoglobulin. It is theorized that the competitive technique is quantitative because the aggregation of abnormal immunoglobulin does not occur in a liquid phase. This difference in the effectiveness of the competitive and direct techniques forms the basis of a qualitative test for the presence of a significant concentration of abnormal homogeneous immunoglobulin. That is, the measurement of immunoglobulin obtained by the competitive technique which is significantly higher than the comparable measurement of the immunoglobulin by the direct technique is a positive indication of the presence of abnormal immunoglobulin. It has been found that if such ratio of competitive to direct technique measurement is in excess of about 2:1, there is a significant quantity of abnormal immunoglobulin present.

Another advantage of the above comparative testing is that the ratio of the readings of the direct technique to that of the competitive technique is an approximation of the proportion of normal immunoglobulin of a particular class as a fraction of the total normal and abnormal immunoglobulin of that class. This is based upon the assumption that essentially the entire signal produced by the direct technique is due to the reaction of only the normal immunoglobulin with the labeled antibody. Although there is some error inherent in this assumption, this test is effective for determining the approximate proportion of normal immunoglobulin in a given class in the presence of a vast excess of abnormal globulin. Comparison of the measurements obtained by the two types of test can be used for determining the effectiveness of treatment such as chemotherapy.

A further disclosure of the nature of the present invention is provided by the following specific examples of the practice of the invention. It should be understood that the data disclosed serve only as examples and are not intended to limit the scope of the invention.

EXAMPLE 1 (Direct Technique)

In the determination of the concentration of human IgG by the direct technique, a serum sample is prediluted in a 1:10 ratio by volume with protein buffer solution at a 0.125% concentration of bovine serum albumin in phosphate buffered saline at pH 7.7±0.1 including a 0.1% sodium azide preservative. 5 microliters of this diluted sample is pipetted into a test tube containing 500 microliters of the above buffer and thoroughly mixed. Then a solid support surface comprising a polymethylmethacrylate polymer disc attached to a holder is immersed into the tube and shaken for 20 minutes to permit sufficient adsorption to occur for subsequent analysis. Thereafter, the disc is transferred to another test tube containing the same protein buffer solution and shaken for 5 minutes to wash unadsorbed antigen from the surface.

Thereafter, the support surface is immersed in an excess of labeled antibody comprising appropriate monospecific fluorescein isothiocyanate (FITC) labeled goat antibody to human IgG, diluted appropriately in phosphate buffered saline at pH 7.5±0.5 containing 0.125% BSA. The support surface is thoroughly mixed by shaking the tube of fluorescent reagent for approximately 10 minutes.

Thereafter, the surface is again washed in a buffer solution comprising phosphate buffered saline at a pH of 7.7±0.1 including a 0.1% sodium azide preservative. The support surface is thoroughly washed with the solution by shaking for 25 minutes. Thereafter, it is read in a fluorometer.

A serum sample without any predilution is treated in an identical manner except monospecific fluorescein isothiocyanate labeled goat antibodies to hum IgA and human IgM are used in determining the concentrations of human IgA and human IgM, respectively.

The fluorescence of the foregoing samples is then compared against reference samples containing known quantities of the immunoglobulin to be quantitated. The base reference samples are prepared from pooled human serum standardized by reference to WHO immunoglobulin reference preparations. Suitable concentrations to form a calibration curve may be found from the following chart:

| Calibrator | mg/dl | | | IU/ml | | |
|---|---|---|---|---|---|---|
| | G | A | M | G | A | M |
| I | 500 | 60 | 40 | 60 | 40 | 50 |
| II | 1200 | 120 | 80 | 150 | 85 | 95 |
| III | 1800 | 240 | 200 | 225 | 170 | 235 |
| IV | 3000 | 480 | 400 | 375 | 340 | 470 |

(The exact concentrations are printed on the label of each Calibrator vial.)

The calibration curve for the direct test is made by carrying out the direct test on each of the four calibrators using exactly the same procedure, i.e., quantities of buffer, antibody, and times but simply substituting calibrator for serum sample. The calibration curve is then prepared by plotting the strength of the fluorescent signals for the several calibrators against the immunoglobulin concentration of the calibrator. The curve is conveniently made by using the fluorescent signal value as the ordinate and the concentration or the logarithm of the concentration of the immunoglobulin (IgG, IgA or IgM as the case may be) as the abscissa. The sample concentration is obtained by finding the strength of its fluorescent signal on the ordinate, moving horizontally to the curve and then downwardly to the concentration scale on the abscissa.

EXAMPLE 2 (Competitive Technique)

In the determination of the concentration of human IgG by the competitive technique, a serum sample is prediluted in the manner set forth in Example 1. Then, labeled antibody comprising appropriate monospecific FITC labeled goat antibody to human IgG, diluted as in Example 1, is added to 0.5 ml of the same serum sample as in Example 1 in a test tube. Then, the tube is thoroughly mixed by shaking for approximately 20 minutes to incubate the antigen and excess labeled antibody.

A solid support surface of the type in Example 1 is coated with normal heterogeneous IgG by immersing the surface in a calibrator serum sample of the foregoing type in a concentration of 200 mg/dl. The surface is shaken in a tube of the calibrator for about 20 minutes to permit sufficient adsorption to occur for subsequent analaysis. Thereafter, the surface is transferred to another test tube containing protein buffer solution and shaken for 5 minutes to wash unadsorbed immunoglobulin from the surface.

Then, the support surface is immersed in the test tube containing incubated serum IgG and antibody to permit excess antibody which has not reached with the IgG of the serum sample to immunologically react with the IgG on the support surface. During this second stage of incubation, the support surface is thoroughly mixed by shaking the tube for approximately 10 minutes. Thereafter, the surface is again washed as set forth above and read by a fluorometer.

A second calibration curve is prepared by carrying out the competitive procedure with each of the above-described calibrator solutions using the same quantities and times as those employed with the sample serum. The curve is prepared by plotting the fluorescent signals against the immunoglobulin concentrations of the calibrators in the manner described for preparation of the calibrator curve for the direct test and the concentration of the immunoglobulin is found by locating the strength of the sample fluorescent signal on the ordinate, moving horizontally to the corresponding point on the curve and then moving vertically downward to the concentration scale on the ordinate.

The measured quantity of IgG by the direct method (Example 1) is then compared to that of the indirect method (Example 2). If the ratio of the indirect measurement to the direct measurement is in excess of about 2:1, then the presence of significant abnormal homogeneous immunoglobulin is indicated.

EXAMPLES 3–22

A series of runs were performed on a number of serum samples using a direct technique from Example 1 and the competitive technique of Example 2 on each sample.

The same samples were assayed by an RID technique of a conventional type such as disclosed in the immunoglobulin test kit identified as Engoplate distributed by Kallestad of Chaska, Mn., identified on the test kit insert as 7G70. Briefly summarized, measured portions of equal volumes of the serum samples are placed in precisely dimensioned wells punched in a layer of agarose containing a monospecific antibody. The immunoglobulin diffuses radially through the gel forming a precipitin ring with the antibodies. Ring diameters are measured at the point where immunoglobulin concentration has been reduced and immunoglobulin-antibody complexing has reached equivalence (end point method). Alternatively, ring diameters are measured before equivalence is reached (timed diffusion method). These results are compared against reference curves for the RID method.

The results of Examples 3–22 are set forth in the following table.

TABLE

| | | IgGAM Values of Monoclonal Proteins | | | | | | |
|---|---|---|---|---|---|---|---|---|
| Serum No. | Type (Ig) | G | A | M | (Direct) G | A | M | Indirect Assay |
| 3 | G | 2650 | 22 | 66 | 610 | 68 | 75 | G- 2400 |
| 4 | G | 7250 | 43 | 21 | 820 | 53 | 22 | G- 7500 |
| 5 | G | 4500 | 22 | 36 | 300 | 36 | 22 | G- 3800 |
| 6 | G | 3870 | 30 | 21 | 2000+ | 28 | 8 | G- 3600 |
| 7 | G | 5000 | 87 | 110 | | 140 | 57 | G- 4200 |
| 8 | G | 5400 | 37 | 30 | 1075 | 38 | 24 | G- 4000 |
| 9 | G | 2100 | 97 | Too Low | Saturate | | 88 | 30 G- 17,500 |
| 10 | A | 730 | 2190 | 66 | 750 | 390 | 76 | A- 1575 |
| 11 | A | 560 | 2600 | 57 | 800 | 400 | 75 | A- 3000 |
| 12 | A | 440 | 10,650 | 22 | 600 | 65 | 12 | A- 3600 |
| 13 | M | 620 | 36 | 1680 | 690 | 60 | 260 | M- 1600 |
| 14 | G | 4400 | 38 | 34 | 1640 | 46 | 22 | G- 3750 |
| 15 | G | 1690 | 101 | 74 | 930 | 120 | 57 | G- 2010 |
| 16 | G | 3020 | 30 | 18 | 530 | 47 | 17 | G- 7300 |
| 17 | A | 255 | 770 | 18 | 750 | 490 | 15 | A- 1850 |
| 18 | A | 650 | 680 | 120 | 850 | 240 | 84 | A- 465 |
| 19 | A | 1050 | 800 | 135 | 1280 | 500 | 61 | A- 775 |
| 20 | A | 750 | 1620 | 63 | 780 | 140 | 37 | A- 900 |
| 21 | M | 290 | 22 | 630 | 530 | 25 | 1180+ | M- 3790 |
| 22 | M | 1750 | 155 | 1220 | 960 | 165 | 180 | M- 1550 |

It is apparent by comparing the assay obtained by the indirect technique to that obtained by the direct technique that all sera except numbers 6, 18 and 19 show a ratio greater than 2 to 1. All of these examples are positive indications of abnormal immunoglobulin in the serum which is indicative of myeloma. Examples 6, 18 and 19, being below said ratio are negative tests for myeloma.

The terms and expressions which have been employed here are used as terms of description and not of limitations, and there is no intention, in the use of such terms and expressions, of excluding equivalents of the features shown and described, or portions thereof, it being recognized that various modifications are possible with the scope of the invention claimed.

What is claimed is:

1. The method of determining the presence of clinically significant quantities of abnormal homogeneous immunoglobulin in liquid human serum sample which comprises
   I. (a) sorbing immunoglobulin from a first fraction of said serum onto an immunological unreactive solid sorptive surface, and then
   (b) contacting said sorptive surface with an aqueous reagent containing an excess of labeled antibody specifically reactive with sample immunoglobulin,
   (c) washing said sorptive surface,
   (d) measuring the quantity of labeled antibody held on said surface,
   II. (a) sorbing normal heterogeneous immunoglobulin onto a second immunologically unreactive solid sorptive surface,
   (b) mixing an excess of labeled antibody specifically reactive with sample immunoglobulin with a second fraction of said serum,
   (c) contacting the solid support surface from IIa with a mixture of IIb, then
   (d) washing said second surface,
   (e) measuring the quantity of labeled antibody held on said second surface;
   (f) determining the ratio of the measurements obtained in steps IIe and Id, a ratio in excess of 2:1 being indicative of the presence of clinically significant quantities of abnormal immunoglobulin in the serum sample.

2. The method of claim 1 in which said labelled antibody is labelled with a material selected from the group consisting of a luminescent substance, a radioactive substance, an enzyme or metal containing substance.

3. The method of claim 1 in which the labelled antibody is labelled with a fluorogen.

4. The method of claim 1 in which said sample includes significant quantities of protein other than the antigen or antibody to be quantitated, and wherein a predetermined quantity of buffer protein unreactive with said labelled antigen or antibody at a concentration in excess of the antigen or antibody concentration of said sample is added to said sample prior to step Ia and IIa to minimize the dependence of sorbed antibody or antigen to be quantitated upon variations in the content of said other protein in said sample.

5. The method of claim 1 in which said support surfaces are selected from the group consisting of a polymeric substrate, silica gel, silicone wafers, glass, insoluble proteins, and a metallic surface.

* * * * *